US012773680B2

(12) United States Patent
Yoshioka et al.

(10) Patent No.: US 12,773,680 B2
(45) **Date of Patent: *Oct. 27, 2026**

(54) LACTIC ACID ADSORBENT AND METHOD FOR REMOVING LACTIC ACID

(71) Applicants: NIKKISO CO., LTD., Tokyo (JP); TOHOKU UNIVERSITY, Sendai (JP)

(72) Inventors: Toshiaki Yoshioka, Sendai (JP); Tomohito Kameda, Sendai (JP); Fumihiko Kitagawa, Kanazawa (JP); Yoichi Jimbo, Kanazawa (JP); Masayuki Kondo, Kanazawa (JP)

(73) Assignees: NIKKISO CO., LTD., Tokyo (JP); TOHOKU UNIVERSITY, Sendai (JP)

( * ) Notice: Subject to any disclaimer, the term of this patent is extended or adjusted under 35 U.S.C. 154(b) by 1159 days.

This patent is subject to a terminal disclaimer.

(21) Appl. No.: 17/741,871

(22) Filed: May 11, 2022

(65) Prior Publication Data

US 2022/0266220 A1 Aug. 25, 2022

Related U.S. Application Data

(63) Continuation of application No. PCT/JP2020/041749, filed on Nov. 9, 2020.

(30) Foreign Application Priority Data

Nov. 13, 2019 (JP) ................................ 2019-205427

(51) Int. Cl.
*B01J 20/24* (2006.01)
*B01J 20/02* (2006.01)
(Continued)

(52) U.S. Cl.
CPC ........... *B01J 20/24* (2013.01); *B01J 20/0248* (2013.01); *B01J 20/0296* (2013.01);
(Continued)

(58) Field of Classification Search
None
See application file for complete search history.

(56) References Cited

U.S. PATENT DOCUMENTS

2007/0275244 A1* 11/2007 Handrosch ............ A61K 8/466 427/372.2
2021/0170359 A1* 6/2021 Yoshioka .............. B01J 20/041
(Continued)

FOREIGN PATENT DOCUMENTS

CN 111001375 A 4/2020
EP 3848115 A1 7/2021
(Continued)

OTHER PUBLICATIONS

Arus et al., "Ultrasound Intensification of Lactic Fermentation Process in the Presence of Anionic Clays" Rev Chim vol. 65 No. 8 pp. 940-947 (Year: 2014).*
(Continued)

*Primary Examiner* — Andrea Olson
(74) *Attorney, Agent, or Firm* — MUNCY, GEISSLER, OLDS & LOWE, P.C.

(57) ABSTRACT

A lactic acid adsorbent includes a layered double hydroxide that contains multiple metal hydroxide layers and also contains anions and water molecules held between the metal hydroxide layers. The anions include (i) an amino acid such as glutamine, (ii) a dipeptide constituted by one or two kinds of amino acids such as glutamine, (iii) a vitamin such as ascorbic acid 2-phosphate, (iv) a pH buffer such as MES, (v) a glucose metabolite such as pyruvic acid, or (vi) inorganic ions selected from a group including $NO_3^-$ and $Cl^-$.

1 Claim, 4 Drawing Sheets

| | $CO_3$-TYPE Mg-Al LDH | Cl-TYPE Mg-Al LDH | $NO_3$-TYPE Mg-Al LDH | HEPES-TYPE Mg-Al LDH |
|---|---|---|---|---|
| ADSORBENT CONCENTRATION (g/mL) | 0.025 | | | |
| LACTIC ACID ADSORPTION RATE (%) | 0 | 45 | 68 | 73 |
| GLUCOSE ADSORPTION RATE (%) | 5 | 2 | 8 | 17 |

(51) Int. Cl.

| | |
|---|---|
| ***B01J 20/04*** | (2006.01) |
| ***B01J 20/22*** | (2006.01) |
| ***C01F 7/784*** | (2022.01) |
| ***C07H 1/08*** | (2006.01) |

(52) U.S. Cl.

CPC ........... *B01J 20/041* (2013.01); *B01J 20/043* (2013.01); *B01J 20/046* (2013.01); *B01J 20/223* (2013.01); *C01F 7/784* (2022.01); *C07H 1/08* (2013.01); *C01P 2002/22* (2013.01)

(56) References Cited

U.S. PATENT DOCUMENTS

| | | | | |
|---|---|---|---|---|
| 2021/0171904 | A1* | 6/2021 | Kitagawa | C12N 5/0018 |
| 2022/0266216 | A1* | 8/2022 | Yoshioka | B01J 20/30 |
| 2023/0211313 | A1* | 7/2023 | Yoshioka | B01J 20/08<br>210/660 |

FOREIGN PATENT DOCUMENTS

| | | | |
|---|---|---|---|
| JP | S58214338 | A | 12/1983 |
| JP | 2009178682 | A | 8/2009 |
| JP | 2016036804 | A | 3/2016 |
| JP | 2006-281154 | A | 10/2019 |
| JP | 2020184979 | A | 11/2020 |
| WO | WO2015122528 | A | 8/2015 |
| WO | WO2020050068 | | 10/2021 |

OTHER PUBLICATIONS

Choi et al., “Intercalative lon-Exchange Route to Amino Acid Layered Double Hydroxide Nanohybrids and Their Sorption Properties” Eur J Inorg Chem (2015) pp. 925-930, DOI:10.1002/ejic.201403115 (Year: 2015).*

Varga et al., “Cu(II)-amino acid-CaAl-layered double hydroxide complexes, recyclable, efficient catalysts in various oxidative transformations” Journal of Molecular Catalysis A: Chemical vol. 423 pp. 49-60, DOI:10.1016/j.molcata.2016.06.008 (Year: 2016).*

Ziegenheim et al., “Cu(II)Cr(III)-LDH: synthesis, characterization, intercalation properties and a catalytic application” Chemical Papers vol. 72 pp. 897-902, DOI:10.1007/s11696-017-0352-z (Year: 2018).*

U.S. Appl. No. 19/395,938, filed Nov. 20, 2025, Yoshioka, Toshiaki.*

Lili Qin et al., “Two different approaches to synthesizing Mg-Al-layered double hydroxides as folic acid carriers”, Journal of Physics and Chemistry of Solids 69, pp. 2779-2784, 2008.

Melisa Lalikoglu et al., “Investigation of Lactic Acid Seperation by Layered Double Hdroxide: Equilibrium, Kinetics, and Thermodynamics”, Journal of Chemical & Engineering data, Nov. 3, 2015, pp. 3159-3165.

Xiaorui Gao et al., “Intercalation and controlled release properties of vitamin C intercalated layered double hydroxide”, Journal of Solid State Chemistry 203, pp. 174-180, 2013.

Extended European Search Report dated Apr. 12, 2023, Application No. 20888503.8.

* cited by examiner

FIG. 2

| | $CO_3$-TYPE Mg-Al LDH | Cl-TYPE Mg-Al LDH | $NO_3$-TYPE Mg-Al LDH | HEPES-TYPE Mg-Al LDH |
|---|---|---|---|---|
| ADSORBENT CONCENTRATION (g/mL) | 0.025 | | | |
| LACTIC ACID ADSORPTION RATE (%) | 0 | 45 | 68 | 73 |
| GLUCOSE ADSORPTION RATE (%) | 5 | 2 | 8 | 17 |

FIG. 3

| | $CO_3$-TYPE Mg-Al LDH | | |
|---|---|---|---|
| ADSORBENT CONCENTRATION (g/mL) | 0.025 | 0.05 | 0.1 |
| LACTIC ACID ADSORPTION RATE (%) | 0 | 0.6 | 1.8 |
| GLUCOSE ADSORPTION RATE (%) | 5.7 | 3.3 | 11.9 |

| | Cl-TYPE Mg-Al LDH | | |
|---|---|---|---|
| ADSORBENT CONCENTRATION (g/mL) | 0.025 | 0.05 | 0.1 |
| LACTIC ACID ADSORPTION RATE (%) | 9.4 | 11.3 | 17.0 |
| GLUCOSE ADSORPTION RATE (%) | 7.3 | 10.9 | 17.0 |

| | $NO_3$-TYPE Mg-Al LDH | | |
|---|---|---|---|
| ADSORBENT CONCENTRATION (g/mL) | 0.025 | 0.05 | 0.1 |
| LACTIC ACID ADSORPTION RATE (%) | 23.2 | 28.9 | 36.1 |
| GLUCOSE ADSORPTION RATE (%) | 4.8 | 3.1 | 8.3 |

| | HEPES-TYPE Mg-Al LDH | | |
|---|---|---|---|
| ADSORBENT CONCENTRATION (g/mL) | 0.025 | 0.05 | 0.1 |
| LACTIC ACID ADSORPTION RATE (%) | 11.2 | 18.9 | 31.2 |
| GLUCOSE ADSORPTION RATE (%) | 4.1 | 7.9 | 9.7 |

FIG. 4

| | $NO_3$-TYPE Cu-Al LDH | $NO_3$-TYPE Ni-Al LDH | $NO_3$-TYPE Ca-Al LDH | $NO_3$-TYPE Mg-Al LDH | HEPES-TYPE Mg-Al LDH |
|---|---|---|---|---|---|
| CELL PROLIFERATION RATE | 1 | 3.4 | 6.7 | 7.4 | 15.5 |

FIG. 5

| | HEPES-TYPE Mg–Al LDH (Mg/Al RATIO=2.0) | | |
|---|---|---|---|
| ADSORBENT CONCENTRATION (g/mL) | 0.025 | 0.05 | 0.1 |
| LACTIC ACID ADSORPTION RATE (%) | 39.6 | 46.1 | 58.2 |
| GLUCOSE ADSORPTION RATE (%) | 7.9 | 9.8 | 13.3 |

| | CITRIC ACID-TYPE Mg–Al LDH (Mg/Al RATIO=1.8) | | |
|---|---|---|---|
| ADSORBENT CONCENTRATION (g/mL) | 0.025 | 0.05 | 0.1 |
| LACTIC ACID ADSORPTION RATE (%) | 8.8 | 13.0 | 20.4 |
| GLUCOSE ADSORPTION RATE (%) | 8.7 | 12.4 | 14.5 |

| | PYRUVIC ACID-TYPE Mg–Al LDH (Mg/Al RATIO=2.0) | | |
|---|---|---|---|
| ADSORBENT CONCENTRATION (g/mL) | 0.025 | 0.05 | 0.1 |
| LACTIC ACID ADSORPTION RATE (%) | 10.2 | 14.5 | 22.6 |
| GLUCOSE ADSORPTION RATE (%) | 7.3 | 10.1 | 13.3 |

| | L-ALANYL-L-GLUTAMINE-TYPE Mg–Al LDH (Mg/Al RATIO=2.1) | | |
|---|---|---|---|
| ADSORBENT CONCENTRATION (g/mL) | 0.025 | 0.05 | 0.1 |
| LACTIC ACID ADSORPTION RATE (%) | 22.6 | 31.5 | 46.4 |
| GLUCOSE ADSORPTION RATE (%) | 6.7 | 9.6 | 12.8 |

FIG. 6

| | Control | HEPES-TYPE Mg–Al LDH | PYRUVIC ACID-TYPE Mg–Al LDH | CITRIC ACID-TYPE Mg–Al LDH | L-ALANYL-L-GLUTAMINE-TYPE Mg–Al LDH |
|---|---|---|---|---|---|
| CELL PROLIFERATION RATE | 1 | 1.25 | 1.05 | 0.92 | 1.15 |

LACTIC ACID ADSORBENT AND METHOD FOR REMOVING LACTIC ACID

CROSS-REFERENCE TO RELATED APPLICATIONS

This application is based upon and claims the benefit of priority from the prior Japanese Patent Application No. 2019-205427, filed on Nov. 13, 2019, and International Patent Application No. PCT/JP2020/041749, filed on Nov. 9, 2020, the entire content of each of which is incorporated herein by reference.

BACKGROUND

Field of the Invention

The present invention relates to a lactic acid adsorbent and a method for removing lactic acid.

Description of the Related Art

In recent years, in fields such as pharmaceutical manufacturing and regenerative medicine, artificial and efficient mass culture of cells and microorganisms has been required. Examples of cells for which mass culture is required include antibody-producing cells, such as Chinese hamster ovary cells (CHO cells), and pluripotent stem cells, such as embryonic stem cells (ES cells) and induced pluripotent stem cells (iPS cells). If such cells can be stably cultured in large quantities for a long period of time, biological substances, such as monoclonal antibodies, and differentiation induction tissues derived from pluripotent stem cells can be efficiently produced.

As a method for industrially mass culturing cells and microorganisms, suspension stirred culture with use of a culture tank, such as a spinner flask, can be considered. The suspension stirred culture, however, tends to require a large scale of equipment. Therefore, in order to reduce costs, it is effective to increase the culture density of cells and the like. It is, however, known that increasing the culture density suppresses the proliferation of cells and the like. This is because densification of cells and the like increases the concentration of waste products (metabolites) in the culture solution (liquid medium), which reduces proliferative activity of the cells and the like. As a representative waste product that affects cells and the like, lactic acid is known.

Therefore, to stably proliferate cells and the like in a high density condition, it is desirable to remove lactic acid that accumulates in the culture solution. Meanwhile, Patent Literature 1 for example discloses a cell culturing device in which a cell culturing tank and a component-controlling solution tank are connected by a feed line provided with a culture solution component-controlling membrane that allows a component to pass through depending on the concentration difference. In this cell culturing device, the waste products that have accumulated in the culture solution move to the component-controlling solution side, so that the concentration in the culture solution decreases. At the same time, the nutrients, of which the concentration has decreased during the culture process, are replenished such that nutrients in the component-controlling solution are transferred to the culture solution. The environment in the culture solution is thus maintained in a condition suitable for cell culture. As the component-controlling solution, the culture solution itself has been used.

PATENT LITERATURE

Patent Literature 1: WO2015/122528

In the cell culturing device disclosed in Patent Literature 1, waste products are removed from the culture solution using the principle of dialysis. Accordingly, in order to attain sufficient removal of waste products, the capacity of the component-controlling solution tank is set to 10 times or more the capacity of the cell culturing tank. There is therefore a problem that the required liquid amount becomes huge and costly. In particular, when the culture solution itself is used as the component-controlling solution, a large amount of expensive culture medium is consumed, which further increases the cost. In addition, when the waste products are removed using a dialysis technology, there is also a problem that the structure of the culturing device becomes complicated.

Therefore, a novel technology for removing lactic acid using a method other than the dialysis technology has been strongly desired. However, when a lactic acid removal method other than the dialysis technology is used, it should be avoided that the proliferation of cells or microorganisms is restrained by the lactic acid adsorption process itself. Also, high efficiency of lactic acid removal is naturally required to obtain a more favorable growth environment for cells and the like.

SUMMARY OF THE INVENTION

The present invention has been made in view of such a situation, and a purpose thereof is to provide a technology for reducing negative effect on the proliferation of cells or microorganisms caused by lactic acid or lactic acid removal processing.

One aspect of the present invention relates to a lactic acid adsorbent. The lactic acid adsorbent includes a layered double hydroxide that contains multiple metal hydroxide layers and also contains anions and water molecules held between the metal hydroxide layers. The anions include (i) at least one amino acid selected from a group including glutamic acid, aspartic acid, glycine, alanine, valine, leucine, isoleucine, serine, threonine, cysteine, methionine, asparagine, glutamine, phenylalanine, tyrosine, tryptophan, and proline, (ii) a dipeptide constituted by one or two kinds of amino acids selected from the abovementioned group, (iii) at least one vitamin selected from a group including ascorbic acid 2-phosphate and folic acid, (iv) at least one pH buffer selected from a group including MES, Bis-Tris, ADA, PIPES, ACES, MOPSO, BES, MOPS, TES, HEPES, DIPSO, TAPSO, and POPSO, (v) at least one glucose metabolite selected from a group including pyruvic acid, citric acid, ketoglutaric acid, succinic acid, oxaloacetic acid, and fumaric acid, or (vi) inorganic ions of at least one kind selected from a group including $NO_3^-$ and $Cl^-$.

Another aspect of the present invention relates to a method for removing lactic acid. The method for removing includes bringing the lactic acid adsorbent according to the abovementioned aspect into contact with lactic acid.

Optional combinations of the aforementioned constituting elements, and implementation of the present invention, including the constituting elements and expressions, in the form of methods, apparatuses, or systems may also be practiced as additional modes of the present invention.

BRIEF DESCRIPTION OF THE DRAWINGS

Embodiments will now be described, by way of example only, with reference to the accompanying drawings which are meant to be exemplary, not limiting, and wherein like elements are numbered alike in several Figures, in which:

FIG. 2 shows a lactic acid adsorption rate and a glucose adsorption rate of each of layered double hydroxides in an aqueous solution containing lactic acid and glucose;

FIG. 3 shows lactic acid adsorption rates and glucose adsorption rates of each of layered double hydroxides in a cell culture solution;

FIG. 4 shows a cell proliferation rate when each of layered double hydroxides was added to a culture medium;

FIG. 5 shows lactic acid adsorption rates and glucose adsorption rates of each of layered double hydroxides in a cell culture solution; and FIG. 6 shows a cell proliferation rate when each of layered double hydroxides was added to a culture medium.

DETAILED DESCRIPTION OF THE INVENTION

Figure 1A:
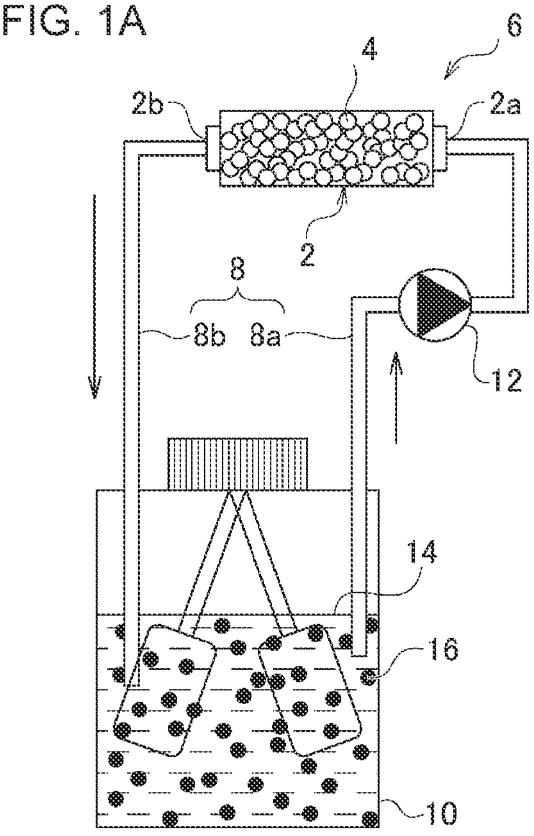
FIGS. 1A-1D are schematic diagrams used to describe methods for removing lactic acid according to an embodiment.

One aspect of the present invention relates to a lactic acid adsorbent. The lactic acid adsorbent includes a layered double hydroxide that contains multiple metal hydroxide layers and also contains anions and water molecules held between the metal hydroxide layers. The anions include (i) at least one amino acid selected from a group including glutamic acid, aspartic acid, glycine, alanine, valine, leucine, isoleucine, serine, threonine, cysteine, methionine, asparagine, glutamine, phenylalanine, tyrosine, tryptophan, and proline, (ii) a dipeptide constituted by one or two kinds of amino acids selected from the abovementioned group, (iii) at least one vitamin selected from a group including ascorbic acid 2-phosphate and folic acid, (iv) at least one pH buffer selected from a group including MES, Bis-Tris, ADA, PIPES, ACES, MOPSO, BES, MOPS, TES, HEPES, DIPSO, TAPSO, and POPSO, (v) at least one glucose metabolite selected from a group including pyruvic acid, citric acid, ketoglutaric acid, succinic acid, oxaloacetic acid, and fumaric acid, or (vi) inorganic ions of at least one kind selected from a group including $NO_3^-$ and $Cl^-$.

In the abovementioned aspect, the metal hydroxide layers may contain divalent metal ions $M^{2+}$ and trivalent metal ions $M^{3+}$, and the divalent metal ions $M^{2+}$ may be $Mg^{2+}$ or $Ca^{2+}$. Also, the lactic acid adsorbent may be brought into contact with a solution containing lactic acid to adsorb lactic acid in the solution. Also, the solution may be a culture solution for cells or microorganisms that contains glucose.

Another aspect of the present invention relates to a method for removing lactic acid. The method for removing includes bringing the lactic acid adsorbent according to any one of the abovementioned aspects into contact with lactic acid.

In the following, the present invention will be described based on a preferred embodiment with reference to the drawings. The embodiment is intended to be illustrative only and not to limit the invention, so that it should be understood that not all of the features or combinations thereof described in the embodiment are necessarily essential to the invention. Like reference characters denote like or corresponding constituting elements, members, and processes in each drawing, and repetitive description will be omitted as appropriate.

Also, the scale or shape of each component shown in each drawing is defined for the sake of convenience to facilitate the explanation and is not to be regarded as limitative unless otherwise specified. Also, when the terms "first", "second", and the like are used in the present specification or claims, such terms do not imply any order or degree of importance and are used to distinguish one configuration from another. Further, in each drawing, part of members less important in describing embodiments may be omitted.

A lactic acid adsorbent according to the present embodiment includes a layered double hydroxide (LDH). A layered double hydroxide contains multiple metal hydroxide layers, and anions and water molecules held between the metal hydroxide layers. The metal hydroxide layers contain divalent metal ions $M^{2+}$ and trivalent metal ions $M^{3+}$ as constituent metals. More specifically, a layered double hydroxide is constituted by: host layers (metal hydroxide layers), which are octahedral layers, positively charged by $M^{3+}$ ions substituting some $M^{2+}$ ions in $M(OH)_2$ containing divalent metal; and guest layers constituted by anions, which compensate for the positive charges in the host layers, and interlayer water. Lactic acid (lactate ions) is adsorbed to a layered double hydroxide through ion exchange with the anions in the guest layers.

A layered double hydroxide is represented by the following chemical formula.

$$[M^{2+}_{1-x}M^{3+}_{x}(OH)_2][A^{n-}_{x/n}\cdot yH_2O]$$

In the above formula, $M^{2+}$ represents a divalent metal ion selected from a group including $Cu^{2+}$, $Mn^{2+}$, $Mg^{2+}$, $Fe^{2+}$, $Ca^{2+}$, $Ni^{2+}$, $Zn^{2+}$, $Co^{2+}$, and $Cd^{2+}$. Also, $M^{3+}$ represents a trivalent metal ion selected from a group including $Al^{3+}$, $Cr^{3+}$, $Fe^{3+}$, $Co^{3+}$, $In^{3+}$, $Mn^{3+}$, and $V^{3+}$. Also, $A^{n-}$ represents an anion in the guest layers. Further, x is from 0.22 to 0.3, n is from 1 to 3, and y is from 1 to 12.

Anions possessed by a layered double hydroxide in the present embodiment include (i) an amino acid, (ii) a dipeptide, (iii) a vitamin, (iv) a pH buffer, (v) a glucose metabolite, or (vi) inorganic ions. Such substances are negatively charged under neutral conditions. The layered double hydroxide may include multiple types of anions.

The amino acid is at least one selected from a group including glutamic acid, aspartic acid, glycine, alanine, valine, leucine, isoleucine, serine, threonine, cysteine, methionine, asparagine, glutamine, phenylalanine, tyrosine, tryptophan, and proline.

The dipeptide is constituted by two kinds of amino acids selected from the group described above. More specifically, the dipeptide is formed by two amino acids of one or two kinds bonded together selected from the group including glutamic acid, aspartic acid, glycine, alanine, valine, leucine, isoleucine, serine, threonine, cysteine, methionine, asparagine, glutamine, phenylalanine, tyrosine, tryptophan, and proline.

The vitamin is at least one selected from a group including ascorbic acid 2-phosphate and folic acid.

The pH buffer is at least one selected from a group including MES (2-morpholinoethanesulfonic acid, monohydrate), Bis-Tris (bis(2-hydroxyethyl)iminotris(hydroxymethyl)methane), ADA (N-(2-acetamido)iminodiacetic acid), PIPES (piperazine-1,4-bis(2-ethanesulfonic acid)), ACES (N-(2-acetamido)-2-aminoethanesulfonic acid), MOPSO (2-hydroxy-3-morpholinopropanesulfonic acid), BES (N,N-bis(2-hydroxyethyl)-2-aminoethanesulfonic acid), MOPS (3-morpholinopropanesulfonic acid), TES (N-tris(hydroxymethyl)methyl-2-aminoethanesulfonic acid), HEPES (2-[4-(2-hydroxyethyl)-1-piperazinyl]ethanesulfonic acid), DIPSO (3-(bis(2-hydroxyethyl)amino)-2-hydroxypropane-1-sulfonic acid), TAPSO (3-[[1,3-dihydroxy-2-(hydroxymethyl)propan-2-yl]amino]-2-hydroxypropane-1-sulfonic acid), and POPSO (piperazine-1,4-bis(2-hydroxy-3-propanesulfonic acid), dihydrate).

The glucose metabolite is at least one selected from a group including pyruvic acid, citric acid, ketoglutaric acid, succinic acid, oxaloacetic acid, and fumaric acid.

The inorganic ions are of at least one kind selected from a group including $NO_3^-$ and $Cl^-$.

When the anions derived from an amino acid, a dipeptide, a vitamin, a pH buffer, or a glucose metabolite are held between the metal hydroxide layers, the toxicity of the layered double hydroxide to cells and the like can be reduced compared to the case where inorganic ions are held. This can restrain the interference of the lactic acid adsorbent itself with the proliferation of cells and the like. Also, when either nitrate ions or chloride ions are used as the anions, the lactic acid adsorption rate can be increased compared to the case where other inorganic ions are held.

The divalent metal ions $M^{2+}$ constituting the metal hydroxide layers may preferably be $Mg^{2+}$ or $Ca^{2+}$ and more preferably be $Mg^{2+}$. Also, the trivalent metal ions $M^{3+}$ constituting the metal hydroxide layers may preferably be $Al^{3+}$. Accordingly, an Mg—Al-based LDH may be more preferable. With this, the toxicity of the layered double hydroxide to cells and the like can be further reduced. Also, multiple types of layered double hydroxides containing different metal ions and anions constituting the layered double hydroxides may be mixed and used.

By bringing a lactic acid adsorbent including a layered double hydroxide described above into contact with lactic acid, the lactic acid can be adsorbed to the layered double hydroxide. In particular, a lactic acid adsorbent of the present embodiment can be suitably used to adsorb and remove lactic acid in a solution. In this case, by bringing the lactic acid adsorbent into contact with a solution containing lactic acid, the lactic acid in the solution can be adsorbed. Also, when the solution is a culture solution for cells or microorganisms that contains glucose, the lactic acid adsorbent can highly selectively adsorb lactic acid to be removed, compared to the glucose to be retained in the culture solution. The type of the culture solution is not particularly limited.

Also, the amount of lactic acid adsorbent added to the solution, i.e., the concentration of the lactic acid adsorbent in the solution, may preferably be more than 0.0005 g/mL, more preferably be 0.005 g/mL or more, further preferably be more than 0.005 g/mL, and yet further preferably be 0.025 g/mL or more. The amount may also preferably be less than 0.2 g/mL and more preferably be 0.1 g/mL or less. By setting the amount of the lactic acid adsorbent to be added to more than 0.0005 g/mL, the lactic acid adsorption rate can be increased more certainly. Also, by setting the amount of the lactic acid adsorbent to be added to less than 0.2 g/mL, the glucose adsorption rate can be kept lower more certainly, so that cells and the like can be cultured more efficiently. The lactic acid adsorption rate is the ratio of the amount of adsorbed lactic acid to the total amount of lactic acid in the solution. Also, the glucose adsorption rate is the ratio of the amount of adsorbed glucose to the total amount of glucose in the solution.

The cells and microorganisms cultured using a culture solution are not particularly limited. For example, cultured cells include: pluripotent stem cells, such as human iPS cells, human ES cells, and human Muse cells, and differentiation induction cells therefrom; somatic stem cells, such as mesenchymal stem cells (MSCs) and nephron progenitor cells; tissue cells, such as human renal proximal tubule epithelial cells, human distal tubule epithelial cells, and human collecting duct epithelial cells; antibody-producing cell lines, such as human fetal renal cells (HEK293 cells); and antibody-producing cell lines derived from animals other than humans, such as Chinese hamster ovary cells (CHO cells) and insect cells (SF9 cells). Since these cells are cells for which mass culture is particularly desired, they are more preferred targets to which the lactic acid adsorbent according to the present embodiment is applied.

Method for Removing Lactic Acid

A method for removing lactic acid according to the present embodiment includes bringing the above-mentioned lactic acid adsorbent into contact with lactic acid (lactate ions). Preferably, the method involves bringing the lactic acid adsorbent into contact with a solution containing lactic acid. The method of bringing the lactic acid adsorbent into contact with lactic acid is exemplified as follows, although not particularly limited thereto. FIG. 1A to FIG. 1D are schematic diagrams used to describe methods for removing lactic acid according to the embodiment. In the following, lactic acid removal from a culture solution will be described as an example. Also, removal of lactic acid from other solutions can be carried out in the same way.

In a first aspect as illustrated in FIG. 1A, an adsorption module 6 including a container 2, such as a column, filled with a lactic acid adsorbent 4 is prepared. The container 2 has an inlet 2*a* and an outlet 2*b* that each communicate with the inside and the outside of the container 2. The lactic acid adsorbent 4 may be in the form of particles, for example. The adsorption module 6 is connected, through a circulation path 8, to a culture vessel 10 such as a spinner flask. The circulation path 8 includes an outward path 8*a* that connects the culture vessel 10 and the inlet 2*a* of the container 2, and a return path 8*b* that connects the outlet 2*b* of the container 2 and the culture vessel 10. On the outward path 8*a*, a pump 12 is connected. The culture vessel 10 contains a culture solution 14 and cells 16. The pump 12 may alternatively be arranged on the return path 8*b*.

When the pump 12 is driven, the culture solution 14 is drawn from the culture vessel 10 and sent into the container 2 of the adsorption module 6 through the outward path 8*a*. The culture solution 14 fed into the container 2 is returned to the culture vessel 10 through the return path 8*b*. In the process of circulating between the culture vessel 10 and the adsorption module 6, the culture solution 14 comes into contact with the lactic acid adsorbent 4 filled in the container 2. In this process, lactic acid in the culture solution 14 is adsorbed by the lactic acid adsorbent 4. Thus, lactic acid in the culture solution 14 is removed. At an end of the outward path 8*a* on the side connected to the culture vessel 10, a filter, not illustrated, is provided. This prevents the cells 16 from flowing toward the adsorption module 6 side. In the process of circulating the culture solution 14 between the culture vessel 10 and the adsorption module 6, the culture solution 14 may be replenished with culture medium components, such as glucose and protein, necessary for the culture of the cells 16.

Thus, in the first aspect, lactic acid in the culture solution 14 is removed by using a culture apparatus equipped with the adsorption module 6 containing the lactic acid adsorbent 4, the culture vessel 10 containing cells or microorganisms and the culture solution 14, and the circulation path 8 connecting the adsorption module 6 and the culture vessel 10 to allow the culture solution 14 to circulate therethrough.

Figure 1B:
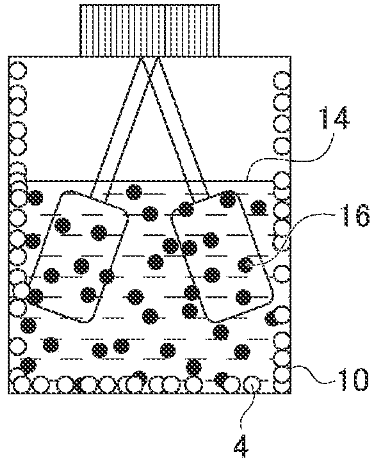

In a second aspect as illustrated in FIG. 1B, the lactic acid adsorbent 4 is supported on the inner wall surface of the culture vessel 10. The culture vessel 10 contains the culture solution 14 and the cells 16. The culture solution 14 therefore comes into contact with the lactic acid adsorbent 4 exposed on the inner wall surface of the culture vessel 10. Thus, the lactic acid in the culture solution 14 can be adsorbed onto the lactic acid adsorbent 4. The culture vessel 10 is exemplified by a spinner flask, petri dish, well plate, cell culture insert, and microsphere.

The method for supporting the lactic acid adsorbent 4 on the inner wall surface of the culture vessel 10 may be a method of bonding the lactic acid adsorbent 4 to the inner wall surface of the culture vessel 10 or may be, when the culture vessel 10 is made of resin, a method of molding the culture vessel 10 from a resin mixed in advance with the lactic acid adsorbent 4, for example. Thus, in the second aspect, lactic acid in the culture solution 14 is removed by using a culture apparatus equipped with the culture vessel 10, and the lactic acid adsorbent 4 supported on the inner wall surface of the culture vessel 10.

Figure 1C:
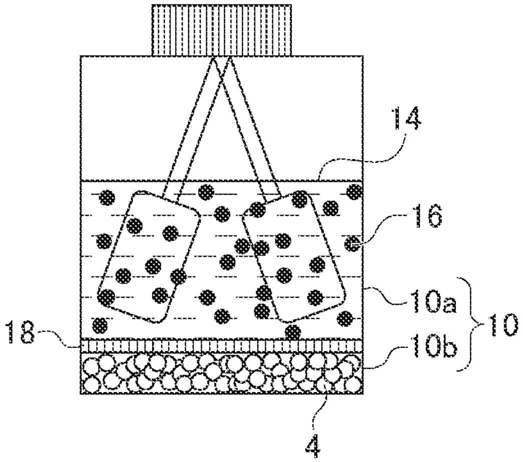

In a third aspect as illustrated in FIG. 1C, the culture vessel 10 has a structure in which the inside of the vessel is divided into an upper part 10*a* and a lower part 10*b* by a diaphragm 18 such as a porous membrane. The culture vessel 10 of this kind is exemplified by a cell culture insert. The upper part 10*a* contains the culture solution 14 and the cells 16, and the lower part 10*b* contains the culture solution 14 and the lactic acid adsorbent 4. The culture solution 14 can move back and forth between the upper part 10*a* and the lower part 10*b* through the diaphragm 18. In contrast, the cells 16 and the lactic acid adsorbent 4 cannot pass through the diaphragm 18.

In such a structure, the culture solution 14 comes into contact with the lactic acid adsorbent 4 contained in the lower part 10*b*. The lactic acid in the culture solution 14 can be therefore adsorbed onto the lactic acid adsorbent 4. Thus, in the third aspect, lactic acid in the culture solution 14 is removed by using a culture apparatus equipped with the culture vessel 10, the lactic acid adsorbent 4, and the diaphragm 18 that divides the inside of the culture vessel 10 into a first space containing the lactic acid adsorbent 4 and a second space containing the cells 16.

Figure 1D:
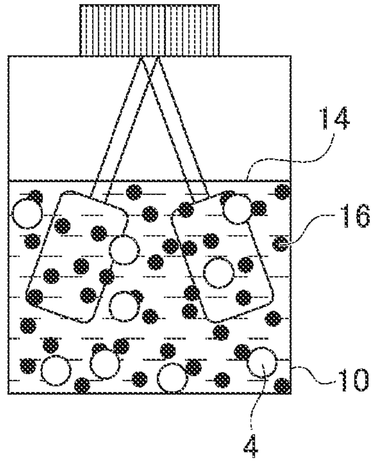

In a fourth aspect illustrated in FIG. 1D, the lactic acid adsorbent 4 in the form of particles is dispersed, precipitated, or suspended in the culture solution 14. Accordingly, the lactic acid in the culture solution 14 can be adsorbed onto the lactic acid adsorbent 4. The lactic acid adsorbent 4 preferably has predetermined size or larger, such as 10 μm or larger, to prevent phagocytosis by the cells 16. Thus, in the fourth aspect, lactic acid in the culture solution 14 is removed by using a culture apparatus equipped with the culture vessel 10, and the lactic acid adsorbent 4 added to the culture solution 14 in the culture vessel 10.

The lactic acid adsorbent is preferably coated with a resin, such as polyvinyl alcohol, a biological gel, such as collagen, alginic acid or gelatin, or the like. This can restrain fine particles that may affect cells and the like from flowing out of the lactic acid adsorbent into the culture solution. Alternatively, the lactic acid adsorbent may be formed by kneading a layered double hydroxide with a ceramic binder, resin binder, biological gel, or the like. This can also restrain the outflow of the fine particles. Examples of the ceramic binder include an alumina binder and colloidal silica. Examples of the resin binder include polyvinyl alcohol and carboxymethyl cellulose. Examples of the biological gel include collagen, alginic acid and gelatin.

When detecting the lactic acid concentration in a solution, it is preferable to use a medium component analyzer, although the method for detection is not particularly limited. The lactic acid concentration can alternatively be detected by using a colorimetric method with a predetermined measuring reagent, an enzyme electrode method utilizing the substrate specificity of an enzyme, high performance liquid chromatography (HPLC), or the like.

As described above, a lactic acid adsorbent according to the present embodiment includes a layered double hydroxide that contains multiple metal hydroxide layers and also contains anions and water molecules held between the metal hydroxide layers. The anions include (i) at least one amino acid selected from a group including glutamic acid, aspartic acid, glycine, alanine, valine, leucine, isoleucine, serine, threonine, cysteine, methionine, asparagine, glutamine, phenylalanine, tyrosine, tryptophan, and proline, (ii) a dipeptide constituted by one or two kinds of amino acids selected from the abovementioned group, (iii) at least one vitamin selected from a group including ascorbic acid 2-phosphate and folic acid, (iv) at least one pH buffer selected from a group including MES, Bis-Tris, ADA, PIPES, ACES, MOPSO, BES, MOPS, TES, HEPES, DIPSO, TAPSO, and POPSO, (v) at least one glucose metabolite selected from a group including pyruvic acid, citric acid, ketoglutaric acid, succinic acid, oxaloacetic acid, and fumaric acid, or (vi) inorganic ions of at least one kind selected from a group including $NO_3^-$ and $Cl^-$. Also, a method for removing lactic acid according to the present embodiment includes bringing the lactic acid adsorbent into contact with lactic acid.

When the anions derived from an amino acid, a dipeptide, a vitamin, a pH buffer, or a glucose metabolite are held between the metal hydroxide layers, the toxicity of the layered double hydroxide to cells and the like can be reduced compared to the case where inorganic ions are held. This can reduce negative effect on the proliferation of cells or microorganisms caused by lactic acid removal processing. Also, when nitrate ions or chloride ions are held as anions between the metal hydroxide layers, the lactic acid adsorption rate can be increased compared to the case where other inorganic ions are held. This can reduce negative effect on the proliferation of cells or microorganisms caused by lactic acid.

Also, according to the present embodiment, unlike the case of removing lactic acid using a conventional dialysis technology, lactic acid can be removed without using a huge amount of solution. Therefore, lactic acid can be removed at low cost. In particular, when the solution is a culture solution for cells or the like, the amount of the culture solution used can be reduced, compared to that in a conventional dialysis technology. Since culture solutions are generally expensive, further cost reduction can be achieved. Also, since lactic acid can be removed only by bringing the lactic acid adsorbent into contact with a solution containing lactic acid, the present embodiment enables simplification of the structure of a culture apparatus.

With the removal of lactic acid, cells or the like can be mass cultured densely. Also, since a decrease in pH in the culture medium caused by lactic acid can be restrained, cells can be mass cultured densely also in this respect. Further, when the cells are pluripotent stem cells, the removal of lactic acid not only enables high-density mass culture of the cells but also can maintain the undifferentiated state of the cells, i.e., the multipotency (pluripotency) of the cells. Therefore, cells suitable for production of biological substances and preparation of differentiation induction tissues can be obtained in large quantities. This can reduce the cost required for pharmaceutical manufacturing and regenerative medicine.

Also, the lactic acid adsorbent of the present embodiment can adsorb lactic acid highly selectively, compared to glucose as a useful component. This enables more efficient cell culture. Therefore, the lactic acid adsorbent of the present embodiment is particularly useful for the removal of lactic acid from a culture solution containing glucose. The lactic acid adsorbent of the present embodiment may also be used in combination with other adsorbents for other cell wastes.

Also, the metal hydroxide layers in the layered double hydroxide contain divalent metal ions $M^{2+}$ and trivalent metal ions $M^{3+}$, and the divalent metal ions $M^{2+}$ may preferably be $Mg^{2+}$ or $Ca^{2+}$. With this, the toxicity of the layered double hydroxide to cells and the like can be further reduced. Therefore, negative effect on the proliferation of cells or microorganisms caused by lactic acid removal processing can be further reduced. Also, the trivalent metal ions $M^{3+}$ constituting the metal hydroxide layers may preferably be $Al^{3+}$.

An embodiment of the present invention has been described in detail. The abovementioned embodiment merely describes a specific example for carrying out the present invention. The embodiment is not intended to limit the technical scope of the present invention, and various design modifications, including changes, addition, and deletion of constituting elements, may be made to the embodiment without departing from the scope of ideas of the invention defined in the claims. Such an additional embodiment with a design modification added has the effect of each of the combined embodiments and modifications. In the aforementioned embodiment, matters to which design modifications may be made are emphasized with the expression of “of the present embodiment”, “in the present embodiment”, or the like. However, design modifications may also be made to matters without such expression. Optional combinations of the abovementioned constituting elements may also be employed as additional aspects of the present invention.

EXAMPLES

Examples of the present invention will now be described by way of example only to suitably describe the present invention and should not be construed as limiting the scope of the invention.

Synthesis of Lactic Acid Adsorbents

Synthesis of $CO_3$-Type Mg—Al LDH

A three-neck flask containing $Na_2CO_3$ was prepared. Under the conditions of nitrogen atmosphere, 30 degrees C., and pH 10.5, ion-exchange water was stirred at 300 rpm while $Mg(NO_3)_2$—$Al(NO_3)_3$ mixed solution (Mg/Al ratio=3.0) was added dropwise thereto. After one hour elapsed from the start of the drop, the reaction solution was filtered and washed with water to obtain the product. The product thus obtained was then dried at 40 degrees C. under reduced pressure for 40 hours to obtain a $CO_3$-type Mg—Al LDH with $CO_3^{2-}$ as the retention ion.

Synthesis of Cl-Type Mg—Al LDH

A three-neck flask containing ion-exchange water was prepared. Under the conditions of nitrogen atmosphere, 30 degrees C., and pH 10.5, the ion-exchange water was stirred at 300 rpm while $MgCl_2$—$AlCl_3$ mixed solution (Mg/Al ratio=3.0) was added dropwise thereto. After one hour elapsed from the start of the drop, the reaction solution was filtered and washed with water to obtain the product. The product thus obtained was then dried at 40 degrees C. under reduced pressure for 40 hours to obtain a Cl-type Mg—Al LDH with $Cl^-$ as the retention ion.

Synthesis of $NO_3$-Type Mg—Al LDH

A three-neck flask containing ion-exchange water was prepared. Under the conditions of nitrogen atmosphere, 30 degrees C., and pH 10.5, the ion-exchange water was stirred at 300 rpm while $Mg(NO_3)_2$—$Al(NO_3)_3$ mixed solution (Mg/Al ratio=3.0) was added dropwise thereto. After one hour elapsed from the start of the drop, the reaction solution was filtered and washed with water to obtain the product. The product thus obtained was then dried at 40 degrees C. under reduced pressure for 40 hours to obtain an $NO_3$-type Mg—Al LDH with $NO_3^-$ as the retention ion.

Synthesis of $NO_3$-Type Ca—Al LDH

A three-neck flask containing ion-exchange water was prepared. Under the conditions of nitrogen atmosphere, 30 degrees C., and pH 12.5, the ion-exchange water was stirred at 300 rpm while $Ca(NO_3)_2$—$Al(NO_3)_3$ mixed solution (Ca/Al ratio=3.0) was added dropwise thereto. After one hour elapsed from the start of the drop, the drop was terminated, and the conditions were changed to nitrogen atmosphere, 80 degrees C., and pH 12.5. After two hours elapsed from the change of conditions, the reaction solution was filtered and washed with water to obtain the product. The product thus obtained was then dried at 40 degrees C. under reduced pressure for 40 hours to obtain an $NO_3$-type Ca—Al LDH with $NO_3^-$ as the retention ion.

Synthesis of $NO_3$-Type Ni—Al LDH

A three-neck flask containing ion-exchange water was prepared. Under the conditions of nitrogen atmosphere, 30 degrees C., and pH 10.5, the ion-exchange water was stirred at 300 rpm while $Ni(NO_3)_2$—$Al(NO_3)_3$ mixed solution (Ni/Al ratio=3.0) was added dropwise thereto. After one hour elapsed from the start of the drop, the reaction solution was filtered and washed with water to obtain the product. The product thus obtained was then dried at 40 degrees C. under reduced pressure for 40 hours to obtain an $NO_3$-type Ni—Al LDH with $NO_3^-$ as the retention ion.

Synthesis of $NO_3$-Type Cu—Al LDH

A three-neck flask containing ion-exchange water was prepared. Under the conditions of nitrogen atmosphere, 30 degrees C., and pH 10.5, the ion-exchange water was stirred at 300 rpm while $Cu(NO_3)_2$—$Al(NO_3)_3$ mixed solution (Cu/Al ratio=3.0) was added dropwise thereto. After one hour elapsed from the start of the drop, the reaction solution was filtered and washed with water to obtain the product. The product thus obtained was then dried at 40 degrees C. under reduced pressure for 40 hours to obtain an $NO_3$-type Cu—Al LDH with $NO_3^-$ as the retention ion.

Synthesis of HEPES-Type Mg—Al LDH (Mg/Al Ratio=3.0)

A three-neck flask containing a HEPES solution (FUJIFILM Wako Pure Chemical Corporation) with a concentration of 3575 mg/L was prepared. Under the conditions of nitrogen atmosphere, 30 degrees C., and pH 10.5, the HEPES solution was stirred at 300 rpm while $Mg(NO_3)_2$—$Al(NO_3)_3$ mixed solution (Mg/Al ratio=3.0) was added dropwise thereto. After one hour elapsed from the start of the drop, the reaction solution was filtered and washed with water to obtain the product. The product thus obtained was then dried at 40 degrees C. under reduced pressure for 40 hours to obtain a HEPES-type Mg—Al LDH with HEPES as the retention ion.

Confirmation of LDH Synthesis

The structures of the compounds (LDHs) obtained through the abovementioned synthesis procedures were confirmed by powder X-ray diffraction using an X-ray diffractometer (RINT-2200VHF, from Rigaku Corporation). In every compound, a peak specific to the LDH was detected. Accordingly, the syntheses of the intended LDHs were ascertained. Further, the composition of each of the compounds was confirmed using an ICP optical emission spectroscopy (iCAP6500 Duo, from Thermo Fisher Scientific Inc.), which supported the compounds as the intended LDHs.

Performance Analyses of Adsorbents in Aqueous Solution (Water-Based Solution) Containing Lactic Acid and Glucose Sodium lactate (Kanto Chemical Co., Inc.) and glucose (FUJIFILM Wako Pure Chemical Corporation) were added to pure water, to prepare an aqueous solution with a glucose concentration of 1000 ppm and a lactic acid concentration of 10 mM. Then, 20 mL each of the aqueous solution was dispensed into multiple 50 mL Erlenmeyer flasks. Also, 0.5 g of various lactic acid adsorbents were added respectively to the aqueous solutions in the Erlenmeyer flasks. Therefore, the concentration of each lactic acid adsorbent was 0.025 g/mL. In the analyses, among the aforementioned lactic acid adsorbents, the $CO_3$-type Mg—Al LDH, the Cl-type Mg—Al LDH, the $NO_3$-type Mg—Al LDH, and the HEPES-type Mg—Al LDH were used.

Each aqueous solution was then stirred at 37 degrees C. and 150 rpm for 24 hours. After 24 hours, the aqueous solution and the lactic acid adsorbent were separated using a 0.1 μm filter. Thereafter, the lactic acid concentration and the glucose concentration in each aqueous solution were measured using an HPLC (JASCO Corporation). Also, the lactic acid adsorption rate and the glucose adsorption rate of each of the adsorbents were calculated based on the following formula.

Adsorption rate (%)=(concentration before adsorption (mM, ppm or mg/dL)−concentration after adsorption (mM, ppm or mg/dL))/concentration before adsorption (mM, ppm or mg/dL)×100

The results are shown in FIG. 2. FIG. 2 shows a lactic acid adsorption rate and a glucose adsorption rate of each of the layered double hydroxides in an aqueous solution containing lactic acid and glucose. As shown in FIG. 2, it was found that the lactic acid adsorption rate was higher in the order of the HEPES type, the $NO_3$ type, the Cl type, and the $CO_3$ type. In particular, the Cl type, the $NO_3$ type, and the HEPES type exhibited significantly high lactic acid adsorption rates compared to the $CO_3$ type. It was also found that each of the Mg—Al LDHs hardly adsorbed glucose in the aqueous solution.

Performance Analyses of Adsorbents in Cell Culture Solution

Sodium lactate (FUJIFILM Wako Pure Chemical Corporation) was added to a pluripotent stem cell medium (StemFit AK02N, from Ajinomoto Co., Inc.) to prepare a culture medium with a glucose concentration of 250 mg/dL and a lactic acid concentration of 10 mM. Then, 20 mL each of the culture medium was dispensed into multiple 50 mL tubes (Thermo Fisher Scientific Inc.). Also, various lactic acid adsorbents were added respectively to the culture media in the tubes. As the lactic acid adsorbents, the $CO_3$-type Mg—Al LDH, the Cl-type Mg—Al LDH, the $NO_3$-type Mg—Al LDH, and the HEPES-type Mg—Al LDH were used. The amount of each lactic acid adsorbent added (concentration) was set to 0.5 g (0.025 g/mL), 1.0 g (0.05 g/mL), and 2.0 g (0.1 g/mL).

Each culture medium was then shaken at 37 degrees C. and 60 times/min for 24 hours. After 24 hours, the culture medium and the lactic acid adsorbent were separated using a 0.22 μm filter. Thereafter, the lactic acid concentration and the glucose concentration in each culture medium were measured using a blood gas analyzer (ABL800 FLEX, from Radiometer Medical ApS). Also, the lactic acid adsorption rate and the glucose adsorption rate of each of the lactic acid adsorbents were calculated based on the aforementioned formula.

The results are shown in FIG. 3. FIG. 3 shows lactic acid adsorption rates and glucose adsorption rates of each of the layered double hydroxides in a cell culture solution. As shown in FIG. 3, although the adsorption rates were somewhat lower than those in the water-based solution, it was found that each of the Cl-type LDH, the $NO_3$-type LDH, and the HEPES-type LDH is capable of adsorbing lactic acid also in a cell culture solution. In particular, the $NO_3$ type and the HEPES type exhibited higher lactic acid adsorption rates than the Cl type. It was also found that the $NO_3$ type and the HEPES type hardly adsorbed glucose in the culture medium.

Toxicity Evaluation of Lactic Acid Adsorbents

Thereafter, 20 mL each of a pluripotent stem cell medium (StemFit AK02N, from Ajinomoto Co., Inc.) was dispensed into multiple containers. Then, 0.5 g of various lactic acid adsorbents were added respectively to the culture media and mixed, and the resulting mixtures were left to stand at 4 degrees C. for 24 hours. Therefore, the concentration of each lactic acid adsorbent was 0.025 g/mL. As the lactic acid adsorbents, the $NO_3$-type Cu—Al LDH, the $NO_3$-type Ni—Al LDH, the $NO_3$-type Ca—Al LDH, the $NO_3$-type Mg—Al LDH, and the HEPES-type Mg—Al LDH were used. After 24 hours, the culture medium and the lactic acid adsorbent were separated using a 0.22 μm filter.

Into six well plates (Corning Incorporated) coated with the culture substrate iMatrix-511, 5 ml each of the culture media were respectively dispensed. Thereafter, in each of the six well plates, 20000 human iPS cells (201B7 cell line: Takahashi K, et al. (2007) Cell) were seeded and cultured for 120 hours. Each culture medium was replaced every 24 hours. After 120 hours elapsed, the human iPS cells were detached by enzyme treatment, and the number of cells in each culture medium was measured using the TC20 Automated Cell Counter (Bio-Rad Laboratories, Inc.). Also, the cell proliferation rate in each culture medium was calculated based on the following formula.

Cell proliferation rate (%)=(number of cells after culture−number of seeded cells)/number of seeded cells×100

The results showed that the cell proliferation rate in the culture medium with the $NO_3$-type Cu—Al LDH added thereto was the lowest. Based on the cell proliferation rate of the $NO_3$-type Cu—Al LDH, the ratio of the cell proliferation rate (hereinafter, simply referred to as the cell proliferation rate) in each of the culture media with the other layered double hydroxides added respectively thereto was calculated. The results are shown in FIG. 4. FIG. 4 shows a cell proliferation rate when each of the layered double hydroxides was added to a culture medium. As shown in FIG. 4, it was found that, among the LDHs with the same retention ion of $NO_3^-$, the cell proliferation rate was higher in the order of the Mg—Al-based LDH, the Ca—Al-based LDH, the Ni—Al-based LDH, and the Cu—Al-based LDH. It was also found that, although the both belong to the same Mg—Al-based type, the layered double hydroxide with the retention ion of HEPES exhibited a higher cell proliferation rate than the layered double hydroxide with the retention ion of $NO_3^-$.

From the above, it was found that a layered double hydroxide holding, as anions, inorganic ions, such as $Cl^-$ and $NO_3^-$, or anions derived from a pH buffer, such as HEPES, has excellent lactic acid adsorption capacity both in an aqueous lactic acid solution and in a culture medium. It was also found that the layered double hydroxide adsorbs lactic acid highly selectively compared to glucose. In particular, it was found that a layered double hydroxide holding $NO_3^-$ or HEPES adsorbs lactic acid further highly selectively in a culture solution. Therefore, it was confirmed that such layered double hydroxides are more suitable for the removal of lactic acid from a culture medium containing glucose.

It was also confirmed that using $Mg^{2+}$ or $Ca^{2+}$ ions, which are major metal ions included in culture mediums, as constituent metal of the metal hydroxide layers can reduce the negative effect on the proliferation of cells and the like. In addition, it was also confirmed that a layered double hydroxide with a pH buffer, such as HEPES, as the retention ion can further reduce the negative effect on the proliferation of cells and the like, compared to the case of inorganic ions as the retention ion. From these results, it can be understood that using a component included in a culture medium, such as an amino acid, a dipeptide, a vitamin, or a glucose metabolite, as the retention ion of a layered double hydroxide can also increase the cell proliferation rate.

Analyses of Adsorbent Performance and Toxicity of Other Lactic Acid Adsorbents

The adsorbent performance and toxicity was evaluated also for the following lactic acid adsorbents.

Synthesis of Lactic Acid Adsorbents

Synthesis of HEPES-type Mg—Al LDH (Mg/Al ratio=2.0)

A three-neck flask containing a HEPES solution (FUJIFILM Wako Pure Chemical Corporation) with a concentration of 3575 mg/L was prepared. Under the conditions of nitrogen atmosphere, 30 degrees C., and pH 10.5, the HEPES solution was stirred at 300 rpm while $Mg(NO_3)_2$—$Al(NO_3)_3$ mixed solution (Mg/Al ratio=2.0) was added dropwise thereto. After one hour elapsed from the start of the drop, the reaction solution was filtered and washed with water to obtain the product. The product thus obtained was then dried at 40 degrees C. under reduced pressure for 40 hours to obtain a HEPES-type Mg—Al LDH.

Synthesis of Pyruvic Acid-Type Mg—Al LDH

A three-neck flask containing a pyruvic acid solution (FUJIFILM Wako Pure Chemical Corporation) was prepared. Under the conditions of nitrogen atmosphere, 30 degrees C., and pH 10.5, the pyruvic acid solution was stirred at 300 rpm while $Mg(NO_3)_2$—$Al(NO_3)_3$ mixed solution (Mg/Al ratio=2.0) was added dropwise thereto. After one hour elapsed from the start of the drop, the reaction solution was filtered and washed with water to obtain the product. The product thus obtained was then dried at 40 degrees C. under reduced pressure for 40 hours to obtain a pyruvic acid-type Mg—Al LDH.

Synthesis of Citric Acid-Type Mg—Al LDH

A three-neck flask containing a citric acid solution (FUJIFILM Wako Pure Chemical Corporation) was prepared. Under the conditions of nitrogen atmosphere, 30 degrees C., and pH 10.5, the citric acid solution was stirred at 300 rpm while $Mg(NO_3)_2$—$Al(NO_3)_3$ mixed solution (Mg/Al ratio=2.0) was added dropwise thereto. After one hour elapsed from the start of the drop, the reaction solution was filtered and washed with water to obtain the product. The product thus obtained was then dried at 40 degrees C. under reduced pressure for 40 hours to obtain a citric acid-type Mg—Al LDH.

Synthesis of L-Alanyl-L-Glutamine-Type Mg—Al LDH

A three-neck flask containing an L-alanyl-L-glutamine solution (FUJIFILM Wako Pure Chemical Corporation) as a dipeptide solution was prepared. Under the conditions of nitrogen atmosphere, 30 degrees C., and pH 10.5, the L-alanyl-L-glutamine solution was stirred at 300 rpm while $Mg(NO_3)_2$—$Al(NO_3)_3$ mixed solution (Mg/Al ratio=2.0) was added dropwise thereto. After one hour elapsed from the start of the drop, the reaction solution was filtered and washed with water to obtain the product. The product thus obtained was then dried at 40 degrees C. under reduced pressure for 40 hours to obtain an L-alanyl-L-glutamine-type Mg—Al LDH.

Confirmation of LDH Synthesis

The structures of the compounds (LDHs) obtained through the abovementioned synthesis procedures were confirmed by powder X-ray diffraction using an X-ray diffractometer (RINT-2200VHF, from Rigaku Corporation). In every compound, a peak specific to the LDH was detected. Accordingly, the syntheses of the intended LDHs were ascertained. Further, the composition of each of the compounds was confirmed using an ICP optical emission spectroscopy (iCAP6500 Duo, from Thermo Fisher Scientific Inc.), which supported the compounds as the intended LDHs.

Performance Analyses of Adsorbents in Cell Culture Solution

Lithium lactate (FUJIFILM Wako Pure Chemical Corporation) was added to a pluripotent stem cell medium (StemFit AK02N, from Ajinomoto Co., Inc.) to prepare a culture medium with a glucose concentration of 250 mg/dL and a lactic acid concentration of 10 mM. Then, 20 mL each of the culture medium was dispensed into multiple 50 mL tubes (Thermo Fisher Scientific Inc.). Also, various lactic acid adsorbents were added respectively to the culture media in the tubes. As the lactic acid adsorbents, the HEPES-type Mg—Al LDH (Mg/Al ratio=2.0), the pyruvic acid-type Mg—Al LDH, the citric acid-type Mg—Al LDH, and the L-alanyl-L-glutamine-type Mg—Al LDH were used. The amount of each lactic acid adsorbent added (concentration) was set to 0.5 g (0.025 g/mL), 1.0 g (0.05 g/mL), and 2.0 g (0.1 g/mL).

Each culture medium was then shaken at 37 degrees C. and 60 times/min for 24 hours. After 24 hours, the culture medium and the lactic acid adsorbent were separated using a 0.22 μm filter. Thereafter, the lactic acid concentration and the glucose concentration in each culture medium were measured using a blood gas analyzer (ABL800 FLEX, from Radiometer Medical ApS). Also, the lactic acid adsorption rate and the glucose adsorption rate of each of the lactic acid adsorbents were calculated based on the aforementioned formula.

The results are shown in FIG. 5. FIG. 5 shows lactic acid adsorption rates and glucose adsorption rates of each of the layered double hydroxides in a cell culture solution. As shown in FIG. 5, it was found that each of the HEPES-type LDH (Mg/Al ratio=2.0), the pyruvic acid-type LDH, the citric acid-type LDH, and the L-alanyl-L-glutamine-type LDH is capable of adsorbing lactic acid in a cell culture solution. Also, in comparison with the results shown in FIG. 3, it was found that a higher lactic acid adsorption rate was obtained by using the HEPES-type Mg—Al LDH (Mg/Al ratio=2.0), compared to the case of using the HEPES-type Mg—Al LDH (Mg/Al ratio=3.0).

Toxicity Evaluation of Lactic Acid Adsorbents

Into multiple 50 mL tubes, 20 mL each of a pluripotent stem cell medium (StemFit AK02N, from Ajinomoto Co., Inc.) was dispensed. Then, 0.5 g of various lactic acid adsorbents were added respectively to the culture media and mixed, and the resulting mixtures were left to stand at 4 degrees C. for 1 hour. Therefore, the concentration of each lactic acid adsorbent was 0.025 g/mL. As the lactic acid adsorbents, the HEPES-type Mg—Al LDH (Mg/Al ratio=2.0), the pyruvic acid-type Mg—Al LDH, the citric acid-type Mg—Al LDH, and the L-alanyl-L-glutamine-type Mg—Al LDH were used. After one hour, the culture medium and the lactic acid adsorbent were separated using a 0.22 μm filter. Meanwhile, as a control, a culture medium containing no lactic acid adsorbent was also prepared.

Into six well plates (Corning Incorporated) coated with the culture substrate iMatrix-511, 5 ml each of the culture media were respectively dispensed. Thereafter, in each of the six well plates, 20000 human iPS cells (201B7 cell line: Takahashi K, et al. (2007) Cell) were seeded and cultured for 120 hours. Each culture medium was replaced every 24 hours. After 120 hours elapsed, the human iPS cells were detached by enzyme treatment, and the number of cells in each culture medium was measured using the TC20 Automated Cell Counter (Bio-Rad Laboratories, Inc.). Also, the cell proliferation rate in each culture medium was calculated based on the aforementioned formula.

The cell proliferation rate of the control was defined as a standard (1), and the ratio of the cell proliferation rate (hereinafter, simply referred to as the cell proliferation rate) in each of the culture media with the lactic acid adsorbents added respectively thereto was calculated. The results are shown in FIG. 6. FIG. 6 shows a cell proliferation rate when each of the layered double hydroxides was added to a culture medium. As shown in FIG. 6, the cell proliferation rate when each lactic acid adsorbent was added was approximately 1. Therefore, it was confirmed that each lactic acid adsorbent hardly shows toxicity to cells.

What is claimed is:

1. A method for removing lactic acid, the method comprising bringing a lactic acid adsorbent into contact with a solution comprising lactic acid and glucose, wherein the lactic acid adsorbent comprises a layered double hydroxide containing a plurality of metal hydroxide layers and anions and water molecules held between the metal hydroxide layers, wherein the anions comprises at least one of:

at least one amino acid selected from the group consisting of glutamic acid, aspartic acid, glycine, alanine, valine, leucine, isoleucine, serine, threonine, cysteine, methionine, asparagine, glutamine, phenylalanine, tyrosine, tryptophan, and proline;

a dipeptide constituted by one or two kinds of amino acids selected from the group consisting of glutamic acid, aspartic acid, glycine, alanine, valine, leucine, isoleucine, serine, threonine, cysteine, methionine, asparagine, glutamine, phenylalanine, tyrosine, tryptophan, and proline;

at least one vitamin selected from the group consisting of ascorbic acid 2-phosphate and folic acid;

at least one pH buffer selected from the group consisting of MES, Bis-Tris, ADA, PIPES, ACES, MOPSO, BES, MOPS, TES, HEPES, DIPSO, TAPSO, and POPSO; or at least one glucose metabolite selected from the group consisting of pyruvic acid, citric acid, ketoglutaric acid, succinic acid, oxaloacetic acid, and fumaric acid, wherein the lactic acid adsorbent is configured to adsorb lactic acid in the solution comprising lactic acid and glucose when the lactic acid adsorbent is brought into contact with the solution.

* * * * *